United States Patent
Hultén

[11] Patent Number: 4,895,516
[45] Date of Patent: Jan. 23, 1990

[54] INTERMEDIATE CERAMIC BONDING LAYER FOR BONDING OF A RESIN TO AN ALLOY STRUCTURE OR SUBSTRUCTURE

[76] Inventor: Johan O. Hultén, 100 E. Bellevue #25D, Chicago, Ill. 60611

[21] Appl. No.: 108,178

[22] Filed: Oct. 14, 1987

[51] Int. Cl.$^4$ .............................................. A61K 6/08
[52] U.S. Cl. .................................... 433/201.1; 427/2; 523/116; 264/16
[58] Field of Search ....................................... 523/116; 433/201.1–210; 427/2; 264/16

[56] References Cited

U.S. PATENT DOCUMENTS

| | | | |
|---|---|---|---|
| 4,364,731 | 12/1982 | Norling et al. | 428/447 X |
| 4,544,359 | 10/1985 | Waknine | 523/116 X |
| 4,547,531 | 10/1985 | Waknine | 523/116 |

*Primary Examiner*—Nancy A. B. Swisher
*Attorney, Agent, or Firm*—Wallenstein, Wagner & Hattis, Ltd.

[57] ABSTRACT

The invention is a method of manufacturing a dental restoration from a polymerizable resin or composite resin with an alloy structure, or a method of manufacturing an alloy substructure-reinforced dental restoration. An alloy structure or substructure is first coated with a liquid, vitrifiable ceramic layer. To ensure against crazing in the ceramic layer upon vitrification, the ceramic and alloy have generally similar coefficients of thermal expansion. After vitrification, the ceramic becomes a ceramic bonding layer. Micropores are then formed on that layer, as by sandblasting or by etching with a suitable etching acid. A silane coupling agent is then applied to the micropore-containing ceramic bonding layer. Finally, the silane coupling agent is overlain with a polymerizable resin or composite resin material, and the resin or composite resin is polymerized.

57 Claims, 1 Drawing Sheet

INTERMEDIATE CERAMIC BONDING LAYER FOR BONDING OF A RESIN TO AN ALLOY STRUCTURE OR SUBSTRUCTURE

DESCRIPTION

TECHNICAL FIELD

The invention relates generally to a method for creating an improved bond between a polymerizable resin or composite resin and a dental crown and bridge alloy structure or substructure. Particularly, the substructures have been treated by application of a ceramic layer, creation of a microporous surface in that layer as by acid etching, applying a silane coupling agent to the micropore-containing ceramic layer, and overlaying and polymerizing the resin or composite resin material onto the silane coupling agent treated layer.

BACKGROUND OF THE INVENTION

Porcelain ceramics have been used in dentistry for several hundred years. They are well known for their ability to mimic the appearance of a natural tooth. In the field of fixed, cemented dental prosthetic restorations, such as crown and bridges, porcelain has commonly been used as a single tooth replacement in the form of a porcelain jacket crown (PJC). A PJC consists entirely of porcelain and is cemented onto a prepared tooth. Due to the mechanical properties of the PJC, it has generally not been used for posterior teeth. In the case of a bridge type of restoration, the porcelain initially consisted of prefabricated and individually adjusted facial veneers fitted to the bridge structure in the wax up stage. After casting the alloy bridge structure, these facial veneers were cemented onto the alloy structure by the use of a zinc-phosphate cement that provided mechanical retention.

In the 1950's the porcelain-fused to-metal restoration was introduced. Generally, a particulate suspension of porcelain ceramic is applied onto a thin pre-oxidized crown and bridge alloy substructure having a compatible coefficient of thermal expansion. The porcelain ceramic is then fired in a furnace. Upon firing, the porcelain is vitrified onto the pre-oxidized surface of the alloy substructure and the materials are bonded together. The bonding mechanism has not yet been completely explained. The shear bond strength of porcelain bonded to an alloy substructure has been reported to be in the neighborhood of 13,000 PSI (Anusavice K., Screening Tests for Metal-Ceramic Systems, p. 373-387. Dental ceramics, Proceedings of the First International Symposium on Ceramics, Quintessence, Chicago, J. W. McLean, ed. 1983).

The porcelain ceramic is generally applied in several layers to achieve a desirable aesthetic effect. The first layer is usually an opaque porcelain ceramic containing a relative high amount of opacifying refractory ceramic material. This layer, commonly called opaque, is most often fired separately and obscures the underlying alloy surface. Thereafter, body and incisal porcelain may be applied by any of several methods, including by "flame spray" technique, or by a "paint-on" or "spray-on" technique, followed by firing.

By utilizing an underlying alloy substructure the porcelain is reinforced in such a way that it is also possible to apply these ceramo-metal restorations in the posterior area of the mouth, and fabricate entire bridges in alloy-reinforced porcelain. Today, the ceramo-metal restoration is perhaps the most common fixed dental prosthetic restoration used. However, despite the many advantages of using porcelain as a dental restorative material, it has some significant drawbacks. Due to its microstructure and hardness, it has a tendency to be highly abrasive on natural dentition, being in opposing contact during mastication. It is brittle, and difficult to successfully repair when fractured in the mouth. Ceramo-metal restorations are also difficult and time consuming to fabricate in the dental laboratory.

Developments and improvements in polymerizable resins and composite resins have enabled these materials to become increasingly attractive as alternative materials for porcelain. However, the mechanical properties of these materials do not allow their use for sole formation of entire permanent fixed restorations. Instead, they are usually either applied as a facial veneering material onto a cast crown and bridge replacement alloy structure, or they are used in combination with a thin, underlying, reinforcing alloy substructure.

Generally, the prior art applications result in structures that are secured either by mechanical or chemical bonding, and they provide generally for a poor resin or composite resin to alloy interface. Each of these known methods may have drawbacks in use or application, or result in a bond which has either inadequate initial strength or a tendency to deteriorate after time. To improve bond strength with these methods, it is conceivable that some of them may be combined.

Mechanical retention may be facilitated by the provision of loops, wires, mesh, beads, or crystals. Such retentions are reviewed in two periodicals, including Shue, Nichols, Townsend, *J. Prosth. Dent.*, Vol. 58, No. 3, September, 1987, pages 297-305; and Naka, C. K., *Gen. Dent.*, July-Aug. 1987, pages 307-310. These mechanical devices are placed in the form of wax or plastic patterns on the wax-up, and cast to form the alloy structure or substructure. The major inherent shortcoming of this and similar methods is that they provide for only mechanical retention between the restoration components. Due to differences in mechanical properties, and to the fact that resins will contract upon polymerization, microscopic gaps may occur at their interfaces. Oral fluids seeping into this gap may cause severe interfacial discoloration or, in extreme cases, a complete delamination of the resin material from the alloy structure or substructure. These types of retentions may compromise the space for the resin or composite resin materials, since they themselves require extensive space.

Mechanical retention without the need for loops or the like is possible through acid etching of the crown and bridge substructure. The alloy structure or substructure is washed with or immersed in acid, and micropores form in the alloy through etching or electrolytical etching. When semi-liquid resin or composite resin material is placed on this substructure, a portion of it enters the micropores. Upon hardening, the material is locked in the micropores and a mechanical bond between the resin or composite resin and the alloy is formed. This method is generally described in Tanaka, Atsuta, Uchiyama, and Kawashima, *J. Prosth. Dent.*, Vol. 42, No. 3, September, 1979, pages 282-291. There are three main disadvantages to this method. First, only predominant base alloys can be utilized, as noble alloys are not etchable in this manner. Second, it is difficult to restrict the acid and the resulting micropore formation to those areas where it is desirable. Third, the bond is purely mechanical.

A chemical bonding method is believed to have been introduced by Musil and Tiller, of Kulzer & Co. GmbH, Wehrheim, Federal Republic of Germany, in 1984. One procedure has been described in Musil and Tiller, *Dent. Labor.*, Vol 32, pages 1155–1161, 1984. This method involves silicoating, i.e., the flame-spray deposition of organic silicone molecules to an alloy structure or substructure. The silicone layer is then treated with a silane coupling agent, which provides the means for formation of the chemical bond. Finally, a polymerizable resin or composite resin is applied to the structure or substructure. This method has questionable long-term durability, as it appears that water attacks the interfacial bond. Particularly, it has been reported that specimens stored for 90 days in 37° C. distilled water lost 30% of their original bond strength. Hero, Ruyter, Waarli, Hultquist, *J. Dent. Res.* 66(8): pages 1380–1385, August, 1987.

Other bonding methods, combining chemical and mechanical bonding, particularly utilizing a composite resin luting cement, are also known. For example, intraoral porcelain-fused-to-metal restorations have been repaired by etching the surface of the porcelain, and then cementing a prefabricated replacement porcelain laminate facing with a composite resin luting cement. A silane coupling agent is used in connection with the composite resin luting cement, apparently to improve retention by providing a chemical bond. Nixon, *Dent. Today.* December, 1986, pages 27 and 31. Nixon teaches that the surface must be contoured with a diamond instrument, that dilute hydrofluoric acid may be used for etching, that at least 75% of the porcelain-fused-to-metal unit should remain after contouring, and that the remaining porcelain-metal unit should be predominantly comprised of porcelain. Methods of porcelain repair using only silane, without etching the porcelain to create micropores in the porcelain surface, were reviewed by Ferrando. In this case a composite restorative material was used instead of a porcelain laminate facing. Calamia and Simonson (IADR, abstract 1095, *J. Dent. Res.*, vol. 63, pages 172–362, 1984) and Stangel, Nathanson, and Hu (*J. Dent. Res.* volume 66, number 9, pages 1460–1465, September, 1987) have also reported on the bond strength of a composite resin luting cement bonded to an etched and silane-treated surface.

A natural tooth may also be restored or altered by first etching the tooth, and then securing a prefabricated porcelain laminate facing to that etched tooth with a composite resin luting cement. Horn, *Dent. Clin. North Am.*, volume 27, pages 671–684, 1983; and Calamia, *N.Y. J. Dent.*, volume 53, pages 255–259, 1983.

To the knowledge of the inventor, none of the prior art teaches a method comprising the application of a thin ceramic layer to act as a bonding medium between a polymerizable resin or composite resin material and a reinforcing alloy substructure, or to a dental crown and bridge alloy structure so as to retain a composite resin veneering material to that structure.

SUMMARY OF THE INVENTION

The method includes first coating a crown and bridge alloy structure or substructure with a thin and vitrifiable ceramic. To ensure a relatively tight-fitting interface and to prevent crazing in the ceramic after it has been fired to the structure or substructure, the crown and bridge alloy structure or substructure and the ceramic have a generally similar coefficient of thermal expansion. The thin, particulate, ceramic coating is next vitrified to form a thin ceramic bonding layer (CBL) on the structure or substructure.

The thin ceramic bonding layer is treated to form micropores in the ceramic surface, as by etching with a suitable etching acid. A silane coupling agent is next applied to the micropore-containing ceramic bonding layer, forming a surface-conditioned ceramic bonding layer (scCBL). Finally, the scCBL is overlain with a polymerizable resin or composite resin material, and the resin or composite resin is polymerized. Both etching and silane coupling agent treatment, independent of each other, promote the formation of a bond between the components.

A suitable ceramic for use in connection with this method is a two-phased feldspathic porcelain ceramic which has a continuous vitreous phase and a dispersed, discontinuous lucite crystal phase. However, it is anticipated that other ceramics may be suitable for the present invention. Among these other ceramics are castable ceramic glass or castable hydroxyapatite. Although the means of application of these latter two particular ceramics in connection with the present invention has not yet been solved, it is believed that either a flame-spray or particulate suspension method or a glass-cast-onto-alloy method will ultimately prove suitable. Any ceramic which is acid etchable, or which by any other means gives a surface morphology which ensures sufficient micropore formation to result in a mechanical bond, is deemed within the scope of the present invention.

Refractory ceramics are often added to porcelains as opacifying agents. To ensure that the porcelain is acid-etchable, the level of these refractory ceramics, such as zirconium, tin oxide, and titanium oxide, should be kept to a minimum to not compromise etchability. For example, with the Austenal Dental brand of Microbond Natural Ceramic Porcelain, it has been observed that refractory ceramics should not exceed from about 5%–29% (wt.) of the porcelain ceramic. The level is believed to be dependant on the composition of the refractory material.

Hydrofluoric acid or a dilute hydrofluoric acid solution is suitable for etching the thin ceramic layer. For example, effective etching has been accomplished by submerging the specimen in an ultrasonic bath containing 10% hydrofluoric acid for 2.5 minutes. However, any etching procedure or any etching acid which provides an etching pattern and a suitable micro morphology ensuring a strong mechanical bond will be acceptable for the present invention.

After etching or micropore formation and when the ceramic bonding layer has been rinsed and dried, a silane coupling agent is applied to its surface to promote a chemical bond with the subsequently applied polymerizable resin or composite resin material. Any of a number of organo-functional silane coupling agents will prove suitable, including gamma-methacryloxypropyl trimethoxysilane, available as "A-174" from the Union Carbide Company. The ceramic surface is typically wetted with a solution of the silane coupling agent and then dried in air. The polymerizable resin or composite resin material is then overlain on the etched, silane-treated CBL, or scCBL.

The present method results in acceptably strong bonding between the resin or composite resin material and the alloy structure or substructure. As will be seen by the results of testing to be discussed hereinafter, the bond between components can be so strong that under stress, a cohesive failure occurs within the thin ceramic bonding layer itself prior to failure or delamination along any of the interfaces between the components.

DETAILED DESCRIPTION OF THE PREFERRED EMBODIMENT

The application of a thin surface conditioned ceramic bonding layer (scCBL) utilizes some of the same general techniques described above for ceramo-metal restorations. However, the scCBL is not intended to act as an overlaying veneering material, but is instead provided to promote the retention of a polymerizable resin or composite resin material and either an alloy structure or substructure.

Figure 1:
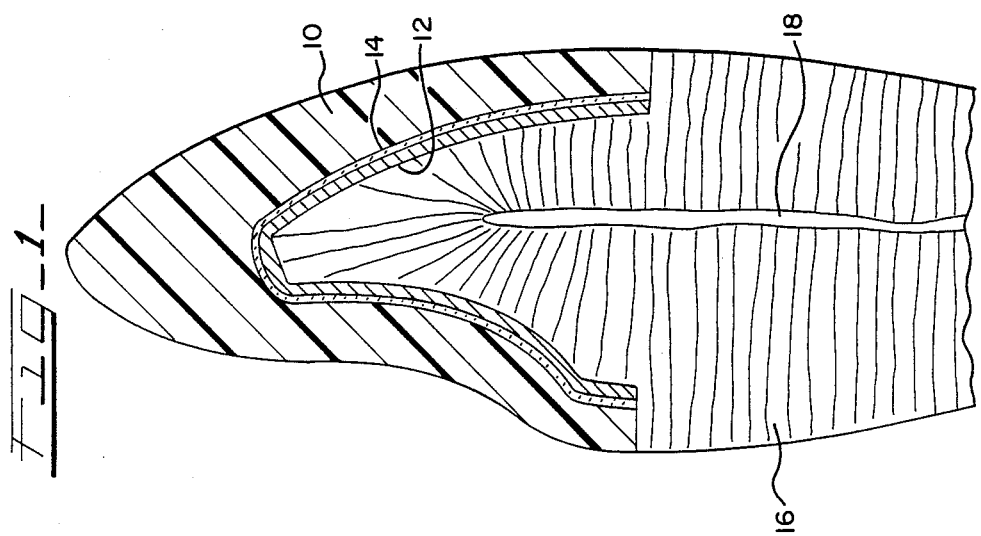
FIG. 1 is a cross-sectional view of a resin or composite resin alloy substructure reinforced dental restoration, using an intermediate surface conditioned ceramic bonding layer (scCBL).

In FIG. 1, one embodiment of the present invention is shown. Particularly, a resin or composite resin 10 is secured to an underlying alloy substructure 12 through the surface condiditoned ceramic bonding layer 14 (scCBL). Also shown in this cross-sectional view are the prepared tooth 16 and the dental nerve 18.

Figure 2:
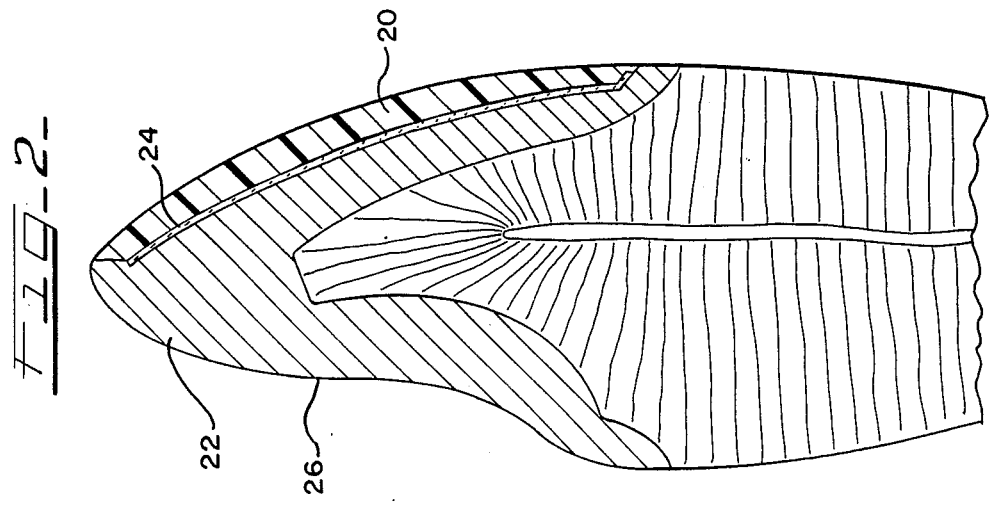
FIG. 2 is a cross-sectional view of a dental crown alloy restoration having a facial resin or composite resin veneering material retained to the underlying structure by means of a surface conditioned ceramic bonding layer (scCBL).

In FIG. 2, another embodiment of the present invention is shown. Particularly, the resin or composite resin 20 is secured to the facial portion of the tooth and to the underlying alloy structure 22 by means of an intermediate surface conditioned ceramic bonding layer 24 (scCBL). While the resin or composite resin are shown extending only to the upper tip of the restoration, it will be understood by those skilled in the art that the claims encompass restorations where the resin or composite resin may extend along its left, inwardly-facing portion 26.

The ceramic is to be applied in an amount that is sufficiently thick so that after sand blasting and acid etching, a thin layer preferably covers the entire desired portion of the structure or substructure. Sandblasting and etching are believed to remove about 25 microns from the thickness of the ceramic layer. Allowing for variations in the thicknesses removed by these processes as typically experienced in the dental laboratory, the ceramic bonding layer (CBL) should be initially applied in an amount not less than 75 to 100 microns. Keeping the ceramic layer as thin as possible, on the other hand, will ensure the maximum available space for the polymerizable resin or composite resin material. Sufficient amounts of polymerizable resin or composite resin material are necessary to ensure acceptable aesthetic appearance of the restoration, and to allow for surface removal from both polishing and intra-oral wear.

It is believed that laboratory technicians will generally manufacture a restoration with a scCBL having a thickness not exceeding 250 microns, and that the average thickness of the scCBL will range from 175 to 200 microns. In the event that the thickness of the scCBL is in excess of that aesthetically desirable, it may be reduced with grinding instruments or the like. However, no definite upper limit can be set regarding the thickness of the scCBL, and in some cases the thickness may be significantly thicker locally without compromising the desired result. However, for practical reasons one should strive to keep it as thin as possible. In a typical 1.5 mm thick (cross-section) resin or composite resin-fused-to-alloy restoration, 0.3–0.5 mm of the space would be occupied by the alloy structure or substructure, 0.1–0.3 mm would be occupied by the scCBL material, and 0.7–1.1 mm would be occupied by the resin or composite resin material.

A study was made to demonstrate that the present method resulted in a composite resin material bonded to an alloy substructure having strong interfacial bonding.

Ten identical specimens, each of the predominant base alloy NP2 TM and measuring 10 mm × 10 mm × 2 mm, were cast. Alloy NP2 TM is available from Austenal Dental, Inc., 5101 South Keeler Avenue, Chicago, Illinois 60632. Each specimen was then ground flat with silicone carbide, grit 230.

The five specimens comprising Group I were then prepared as follows. Each was pre-oxidized in a Ney Mark IV Digital porcelain furnace at from 1400°–2000° F. White, opaque porcelain material, available as Microbond Natural Ceramic, White body Modifier experimental LP1, from Austenal Dental, Inc., was then applied to one flat side of each specimen. The amount of opaque applied to the specimen was that deemed sufficient to result in a specimen having a thin layer of opaque not exceeding 0.3 mm or 300 microns, the specimens were fired in a porcelain furnace, under vacuum, at from 1400° to 1860° F. The resulting thin layer of ceramic is known as a ceramic bonding layer, hereinafter "CBL."

The other flat side of the specimen was secured with a cyano-acrylate adhesive to a metallographic bakelite cylinder that could be mounted plano-parallel with the sliding portion in a shear testing jig.

The CBL was then blasted with 50 micron glass beads at a pressure of 60 psi until the ceramic surface turned uniformly dull and frosty, etched with 10% hydrofluoric acid in a Branson ultrasonic bath for 2.5 minutes, and rinsed with distilled water and air dried. Silane treatment comprised the application of a 2% (vol.) solution of an organofunctional silane coupling agent (A-174 by the Union Carbide Company) and 2% (vol.) n-propyl amine dissolved in cyclohexane. This treatment is generally described in Chen and Brauer, *J. Dent. Res.*, volume 61, no. 12, pages 1439–1443, December, 1982. The wetted surface was allowed to dry in ambient air, and thereafter washed with acetone and air dried. The procedure was repeated three times. After the final acetone rinse and dry, the surface was heat treated at 110° C. for 15 minutes.

The light-curable, composite resin was Bisco Crown and Bridge Composite, obtained from Bisco Company, Chicago, Ill. Gelatine capsules (Eli Lilly #5) having an inner diameter of approximately 4.65 mm were filled with composite resin in slight excess. The capsules were then placed perpendicular to the scCBL surface, and the excess resin was extruded from the capsules. The composite resin was light cured with an Optilux dental curing light (Demetron Research Corporation, Connecticut, U.S.A.) for a total of 60 seconds, 30 seconds from each of two opposing positions.

Finally, the prepared specimens were placed in 37° C. distilled water for 24 hours prior to testing. After removal from the water and before testing, any excess resin material was carefully removed with a scalpel without thereby affecting the bonded composite stub.

The five specimens comprising Group II were prepared by first mounting one flat side with a cyano-acrylate adhesive to bakelite cylinders. The other flat side was then blasted with 50 micron aluminum oxide at a pressure of 60 psi until a uniform, dull frosty surface was obtained, washed in distilled water, and dried in air. The preparation of the Group II specimens was completed by the above-described composite resin application, curing, and 24-hour long specimen retention in distilled tempered water followed by excess removal.

Testing of the Group I and Group II specimens was carried out with a shear testing jig. Each of the bakelite cylinders to which the specimens were secured was individually mounted in the shear testing jig, flush and plano-parallel with its sliding portion. In this manner, the shear force of the testing machine was exerted as close as possible to the bonded surface of each specimen. The jig was placed in an Instron testing machine with a crosshead speed of 0.1 inch per minute. The load upon failure was recorded as follows:

| Group I | Load, lb. | Shear bond strength, psi |
|---|---|---|
| 1 | 51 | 1937 |
| 2 | 61 | 2317 |
| 3 | 48 | 1824 |
| 4 | 75 | 2849 |
| 5 | 52 | 1975 |

| Group II | Load, lb. | Shear bond strength, psi |
|---|---|---|
| 1 | 13 | 495 |
| 2 | 11 | 418 |
| 3 | failure prior to test | |
| 4 | 12 | 456 |
| 5 | 10 | 380 |

From a comparison of the Group I and Group II specimens, it may be seen that specimens having an intermediate ceramic bonding layer demonstrate superior shear bond strength between composite resin and an alloy sub-structure than specimens without such a scCBL.

As an example of a preferred embodiment in accordance with the invention, a single unit substructure coping of a predominant base alloy, as for example Austenal Dental's NP2 TM, was cast. After divesting, the coping was prepared in a standard manner well-known in the art for obtaining a porcelain ceramic layer. The surface of the coping was ground, as with ceramic stones, until a uniform pure alloy was attained. The coping was then pre-oxidized in a Ney Mark IV porcelain furnace at from 1700°-2000° F. A water-based particulate suspension, as for example Microbond Natural Ceramic, White Body Modifier Experimental LP1, available from Austenal Dental, Inc., was then applied to the oxidized substructure coping surface. The amount applied was sufficient so that the thickness of the thin ceramic layer on the substructure coping after condensing was not less than 100 microns nor greater than 500 microns. The coping was then dried and fired under vacuum in a Ney Mark IV Digital porcelain furnace at a temperature of from 1400°-1860° F. The coping was kept at 1860° F. for one minute to ensure effective vitrification of the ceramic.

After checking the thickness of the ceramic bonding layer (CBL) with a Ivanson Instrument thickness gauge, the CBL was blasted with 50 micron glass beads at a pressure of 60 psi until the surface gloss disappeared and the surface instead appeared dull and frosty. The substructure coping was then washed in distilled water and air dried.

The ceramic surface of the specimen was silane treated by applying a cyclohexane solution containing 2% (vol.) of an organofunctional silane coupling agent (A-174, Union Carbide Corporation) and 2% (vol.) n-propyl amine. The wetted surface was then allowed to air dry, and washed in acetone and air dried. The procedure was repeated three times. After the final acetone wash and dry, the coping was heat treated at 110° C. for 15 minutes.

A light curing composite resin was next applied to the scCBL. The light-curable composite resin material, Bisco Crown and Bridge Composite from Bisco Co., was applied with a plastic spatula. The composite resin material was cured sequentially as the restoration was built up. After final curing, the restoration was finished to a natural tooth-like luster with fine diamonds, rubber wheels, pumice, and diamond polishing paste.

The integrity of the restoration was tested by cutting, with a thin diamond Dedeco separating disc, a vertical, incisal groove through the veneering material until the alloy substructure was reached. A stainless steel instrument was used to wedge the composite resin apart until failure. The fragments were inspected with a Bausch & Lomb stereo microscope at a magnification of 25×, and the result was photographed. The inspection and photographs clearly showed that a cohesive fracture occurred within the thin, surface conditioned ceramic bonding layer (scCBL), rather than at either the interface of the ceramic and the alloy surface, or the interface of the ceramic and the composite resin material.

What I claim is:

1. A method of manufacturing a polymerizable resin or composite resin, alloy substructure reinforced dental restoration, comprising:
    (a) coating a crown and bridge alloy substructure with a vitrifiable ceramic, said alloy and said ceramic having generally similar coefficients of expansion;
    (b) vitrifying said ceramic to fuse said ceramic to said substructure, thereby forming a generally thin ceramic bonding layer on said substructure;
    (c) forming a microporous surface on said ceramic bonding layer with an etching acid to obtain a microporous ceramic bonding layer;
    (d) applying a silane coupling agent to said microporous ceramic bonding layer;
    (e) overlaying said silane coupling agent with a polymerizable resin or composite resin material; and
    (f) polymerizing said resin or composite resin material.

2. The method as set forth in claim 1, wherein said ceramic comprises a feldspathic porcelain.

3. The method as set forth in claim 2, wherein said silane coupling agent comprises a cyclohexane solution of 2% (vol.) n-propyl amine and 2% (vol.) gamma methacryloxypropyl trimethoxysilane.

4. The method as set forth in claim 2, wherein a single coating of said ceramic is applied to said alloy substructure.

5. The method as set forth in claim 4, wherein said polymerizable resin or composite resin material is polymerized by light.

6. The method as set forth in claim 1, wherein said ceramic is applied to said substructure as a particulate suspension.

7. The method as set forth in claim 3, wherein said microporous surface is formed with an etching acid which comprises a 10% solution of hydrofluoric acid.

8. The method as set forth in claim 1, wherein said polymerizable resin or composite resin material is polymerized by light.

9. The method as set forth in claim 1, wherein said polymerizable resin or composite resin material is polymerized by light.

10. A method of manufacturing a resin or composite resin alloy reinforced dental restoration, comprising:
  (a) applying a thin coating of a particulate suspension of a vitrifiable, feldspathic ceramic to a high noble, noble or predominantly base alloy substructure, said alloy and said ceramic having generally similar coefficients of thermal expansion;
  (b) vitrifying said ceramic to fuse said ceramic to said substructure to thereby form a generally thin ceramic bonding layer on said substructure;
  (c) acid etching said ceramic bonding layer with a 10% solution of hydrofluoric acid to form a microporous surface on said ceramic bonding layer;
  (d) applying a silane coupling agent to said microporous surface, said agent comprising a cyclohexane solution of 2% (vol.) n-propyl amine and 2% (vol.) gamma methacryloxypropyl trimethoxysilane;
  (e) overlaying said silane coupling agent with a polymerizable resin or composite resin material; and
  (f) polymerizing by light said resin or composite resin material.

11. A dental restoration made by a method comprising:
  (a) coating a crown and bridge alloy substructure with a vitrifiable ceramic, said alloy and said ceramic having generally similar coefficients of thermal expansion;
  (b) vitrifying said ceramic to fuse said ceramic to said substructure, thereby forming a generally thin ceramic bonding layer on said substructure;
  (c) forming a microporous surface on said ceramic bonding layer with an etching acid;
  (d) applying a silane coupling agent to said microporous surface;
  (e) overlaying said silane coupling agent with a polymerizable resin or composite resin material;
  (f) polymerizing said resin or composite resin material.

12. The dental restoration as set forth in claim 11, wherein said ceramic comprises a feldspathic porcelain.

13. The dental restoration as set forth in claim 12, wherein said silane coupling agent comprises a cyclohexane solution of 2% (vol.) n-propyl amine and 2% (vol.) gamma methacryloxypropyl trimethoxysilane.

14. The dental restoration as set forth in claim 12, wherein a single coating of said ceramic is applied to said alloy substructure.

15. The dental restoration as set forth in claim 13, wherein said microporous surface is formed by an etching acid comprising a 10% solution of hydrofluoric acid.

16. The dental restoration as set forth in claim 13, wherein said polymerizable resin or composite resin material is polymerized by light.

17. The dental restoration as set forth in claim 11, wherein said ceramic is applied to said substructure as a particulate suspension.

18. The dental restoration as set forth in claim 11, wherein said polymerizable resin or composite resin material is polymerized by light.

19. A dental restoration made by a method comprising:
  (a) applying a particulate suspension of a thin coating of a vitrifiable, feldspathic ceramic to a crown and bridge alloy substructure, said alloy and said ceramic having generally similar coefficients of thermal expansion;
  (b) vitrifying said ceramic to fuse said ceramic to said substructure to thereby form a generally thin ceramic bonding layer on said substructure;
  (c) acid etching said ceramic bonding layer with a 10% solution of hydrofluoric acid to form a microporous surface on said ceramic bonding layer;
  (d) applying a silane coupling agent to said microporous surface, said agent comprising a cyclohexane solution of 2% (vol.) n-propyl amine and 2% (vol.) gamma methacryloxypropyl trimethoxysilane;
  (e) overlaying said silane coupling agent with a polymerizable resins or composite resin material; and
  (f) polymerizing by light said resin or composite resin material.

20. In a method of bonding a composite resin dental restoration to an alloy substructure, the method including the steps of applying a silane coupling agent to a generally thin ceramic bonding layer having micropores, overlaying the resulting silane coupling agent-treated, microporous surface with a polymerizable resin or composite resin material, and polymerizing said polymerizable resin or composite resin veneering material, the improvement comprising the steps of:
  (a) applying a thin coating of a particulate suspension of a vitrifiable ceramic to a crown and bridge alloy substructure, said alloy and said ceramic having generally similar coefficients of thermal expansion;
  (b) vitrifying said ceramic to fuse said ceramic to said substructure to thereby form said generally thin ceramic bonding layer on said substructure; and
  (c) forming said micropores on said ceramic bonding layer with an etching said.

21. The method as set forth in claim 20, wherein said ceramic is applied to said substructure as a particulate suspension.

22. The method as set forth in claim 20, wherein said ceramic comprises a feldspathic porcelain.

23. The method as set forth in claim 21, wherein said ceramic comprises a feldspathic porcelain.

24. The method as set forth in claim 20, wherein said micropores are formed by acid etching with a 10% solution of hydrofluoric acid.

25. The method as set forth in claim 22, wherein said micropores are formed by acid etching with a 10% solution of hydrofluoric acid.

26. A method of manufacturing a polymerizable resin or composite resin alloy substructure-reinforced dental restoration, comprising:
  (a) coating a crown and bridge alloy substructure with a vitrifiable ceramic, said alloy and said ceramic having generally similar coefficients of expansion;

(b) vitrifying said ceramic to fuse said ceramic to said substructure, thereby forming a generally thin ceramic bonding layer on said substructure;
(c) forming a microporous surface upon said ceramic bonding layer with etching acid, said bonding layer being of a thickness adequate to permit bonding after formation of a microporous surface thereon;
(d) applying a silane coupling agent to said microporous surface;
(e) overlaying said silane coupling agent with a polymerizable acrylic or composite resin material; and
(f) polymerizing said acrylic or composite resin material.

27. The method as set forth in claim 26, wherein said ceramic bonding layer has an initial thickness of from 25 microns to 500 microns.

28. The method as set forth in claim 26, wherein said ceramic bonding layer has an initial thickness of from 175 to 250 microns.

29. The method as set forth in claim 26, wherein said ceramic bonding layer has an initial thickness of from 75 to 100 microns.

30. A method of manufacturing a dental restoration from a polymerizable resin or composite resin and an alloy structure, comprising:
(a) coating said alloy structure with a vitrifiable ceramic, the alloy of said alloy structure and said ceramic having generally similar coefficients of expansion;
(b) vitrifying said ceramic to fuse said ceramic to said alloy structure, thereby forming a generally thin ceramic bonding layer on said structure;
(c) forming a microporous surface on said ceramic bonding layer with an etching acid to obtain a microporous ceramic bonding layer;
(d) applying a silane coupling agent to said microporous ceramic bonding layer;
(e) overlaying said silane coupling agent with a polymerizable resin or composite resin material; and
(f) polymerizing said resin or composite resin material.

31. The method as set forth in claim 30, wherein said ceramic comprises a feldspathic porcelain.

32. The method as set forth in claim 31, wherein said silane coupling agent comprises a cyclohexane solution of 2% (vol.) n-propyl amine and 2% (vol.) gamma methacryloxypropyl trimethoxysilane.

33. The method as set forth in claim 31, wherein a single coating of said ceramic is applied to said alloy structure.

34. The method as set forth in claim 32, wherein said microporous surface is formed with an etching acid which comprises a 10% solution of hydrofluoric acid.

35. The method as set forth in claim 32, wherein said polymerizable resin or composite resin material is polymerized by light.

36. The method as set forth in claim 30, wherein said ceramic is applied to said structure as a particulate suspension.

37. A method of manufacturing a resin or composite resin-alloy dental restoration, comprising:
(a) applying a thin coating of a particulate suspension of a vitrifiable, feldspathic ceramic to a high noble, noble or predominantly base alloy structure, the alloy of said alloy structure and said ceramic having generally similar coefficients of thermal expansion;
(b) vitrifying said ceramic to fuse said ceramic to said structure to thereby form a generally thin ceramic bonding layer on said structure;
(c) acid etching said ceramic bonding layer with a 10% solution of hydrofluoric acid to form a microporous surface on said ceramic bonding layer;
(d) applying a silane coupling agent to said microporous surface, said agent comprising a cyclohexane solution of 2% (vol.) n-propyl amine and 2% (vol.) gamma methacryloxypropyl trimethoxysilane;
(e) overlaying said silane coupling agent with a polymerizable resin or composite resin material; and
(f) polymerizing by light said resin or composite resin material.

38. A dental restoration made by a method comprising:
(a) coating an alloy structure with a vitrifiable ceramic, the alloy of said alloy structure and said ceramic having generally similar coefficients of thermal expansion;
(b) vitrifying said ceramic to fuse said ceramic to said structure, thereby forming a generally thin ceramic bonding layer on said structure;
(c) forming a microporous surface on said ceramic bonding layer with an etching acid;
(d) applying a silane coupling agent to said microporous surface;
(e) overlaying said silane coupling agent with a polymerizable resin or composite resin material; and
(f) polymerizing said resin or composite resin material.

39. The dental restoration as set forth in claim 38, wherein said polymerizable resin or composite resin material is polymerized by light.

40. The dental restoration as set forth in claim 39, wherein said ceramic comprises a feldspathic porcelain.

41. The dental restoration as set forth in claim 40, wherein said silane coupling agent comprises a cyclohexane solution of 2% (vol.) n-propyl amine and 2% (vol.) gamma methacryloxypropyl trimethoxysilane.

42. The dental restoration as set forth in claim 40, wherein a single coating of said ceramic is applied to said alloy structure.

43. The dental restoration as set forth in claim 40, wherein said microporous surface is formed by an etching acid comprising a 10% solution of hydrofluoric acid.

44. The dental restoration as set forth in claim 41, wherein said polymerizable resin or composite resin material is polymerized by light.

45. The dental restoration as set forth in claim 38, wherein said ceramic is applied to said structure as a particulate suspension.

46. A dental restoration made by a method comprising:
(a) applying a particulate suspension of a thin coating of a vitrifiable, feldspathic ceramic to an alloy structure, the alloy of said alloy structure and said ceramic having generally similar coefficients of thermal expansion;
(b) vitrifying said ceramic to fuse said ceramic to said structure to thereby form a generally thin ceramic bonding layer on said structure;
(c) acid etching said ceramic bonding layer with a 10% solution of hydrofluoric acid to form a microporous surface on said ceramic bonding layer;
(d) applying a silane coupling agent to said microporous surface, said agent comprising a cyclohexane solution of 2% (vol.) n-propyl amine and 2% (vol.) gamma methacryloxypropyl trimethoxysilane;
(e) overlaying said silane coupling agent with a polymerizable resin or composite resin material; and
(f) polymerizing by light said resin or composite resin material.

47. In a method of bonding a composite resin to an alloy structure, the method including the steps of applying a silane coupling agent to a generally thin ceramic bonding layer having micropores, overlaying the resulting silane coupling agent-treated, microporous surface with a polymerizable resin or composite resin material, and polymerizing said polymerizable resin or composite resin material, the improvement comprising the steps of:
(a) applying a thin coating of a particulate suspension of a vitrifiable ceramic to an alloy structure, the alloy of said alloy structure and said ceramic having generally similar coefficients of thermal expansion;
(b) vitrifying said ceramic to fuse said ceramic to said structure to thereby form said generally thin ceramic bonding layer on said structure; and
(c) forming said micropores on said ceramic bonding layer with an etching acid.

48. The method as set forth in claim 47, wherein said ceramic is applied to said structure as a particulate suspension.

49. The method as set forth in claim 48, wherein said ceramic comprises a feldspathic porcelain.

50. The method as set forth in claim 49, wherein said micropores are formed by acid etching with a 10% solution of hydrofluoric acid.

51. The method as set forth in claim 47, wherein said ceramic comprises a feldspathic porcelain.

52. The method as set forth in claim 47, wherein said micropores are formed by acid etching.

53. The method as set forth in claim 47, wherein said micropores are formed by acid etching with a 10% solution of hydrofluoric acid.

54. A method of manufacturing a dental restoration from a polymerizable resin or composite resin and an alloy structure, comprising:
(a) coating an alloy structure with a vitrifiable ceramic, the alloy of said alloy structure and said ceramic having generally similar coefficients of expansion;
(b) vitrifying said ceramic to fuse said ceramic to said structure, thereby forming a generally thin ceramic bonding layer on said structure;
(c) forming a microporous surface upon said ceramic bonding layer with an etching acid, said bonding layer being of a thickness adequate to permit bonding after formation of a microporous surface thereon;
(d) applying a silane coupling agent to said microporous surface;
(e) overlaying said silane coupling agent with a polymerizable acrylic or composite resin material; and
(f) polymerizing said acrylic or composite resin material.

55. The method as set forth in claim 54, wherein said ceramic bonding layer has an initial thickness of from 25 microns to 500 microns.

56. The method as set forth in claim 54, wherein said ceramic bonding layer has an initial thickness of from 175 to 250 microns.

57. The method as set forth in claim 54, wherein said ceramic bonding layer has an initial thickness of from 75 to 100 microns.

* * * * *

UNITED STATES PATENT AND TRADEMARK OFFICE
CERTIFICATE OF CORRECTION

PATENT NO. : 4,895,516

DATED : January 23, 1990

INVENTOR(S) : Johan O. Hulten

It is certified that error appears in the above-identified patent and that said Letters Patent is hereby corrected as shown below:

Column 10, Line 48, delete "said" and insert --acid--.

Signed and Sealed this

Sixth Day of August, 1991

Attest:

Attesting Officer

HARRY F. MANBECK, JR.

Commissioner of Patents and Trademarks